(12) United States Patent
Mayer et al.

(10) Patent No.: US 6,750,522 B1
(45) Date of Patent: Jun. 15, 2004

(54) SENSOR ACCOMMODATED IN A HOUSING

(75) Inventors: Felix Mayer, Zurich (CH); Mark Hornung, Zurich (CH)

(73) Assignee: Sensirion AG, Zurich (CH)

( * ) Notice: Subject to any disclaimer, the term of this patent is extended or adjusted under 35 U.S.C. 154(b) by 164 days.

(21) Appl. No.: 10/130,401

(22) PCT Filed: Sep. 6, 2000

(86) PCT No.: PCT/IB00/01250
§ 371 (c)(1),
(2), (4) Date: May 14, 2002

(87) PCT Pub. No.: WO01/40784
PCT Pub. Date: Jun. 7, 2001

(30) Foreign Application Priority Data

Nov. 30, 1999 (CH) .................................. 2191/99

(51) Int. Cl.⁷ .................... H01L 27/14; H01L 29/82; H01L 29/84
(52) U.S. Cl. .................... 257/414; 257/787; 438/55
(58) Field of Search ............... 257/414, 723, 257/724, 433, 787; 438/18, 24, 25, 26, 55

(56) References Cited

U.S. PATENT DOCUMENTS

| | | | | |
|---|---|---|---|---|
| 3,943,557 A | * | 3/1976 | Frazee et al. ............. 338/34 |
| 5,388,443 A | * | 2/1995 | Manaka ................... 73/31.06 |
| 5,652,443 A | * | 7/1997 | Kasai ....................... 257/252 |
| 6,140,144 A | * | 10/2000 | Najafi et al. ............... 438/53 |
| 6,369,435 B1 | * | 4/2002 | Igel ........................ 257/415 |
| 6,649,994 B2 | * | 11/2003 | Parsons ................... 257/470 |

FOREIGN PATENT DOCUMENTS

| | | | | |
|---|---|---|---|---|
| JP | 2-66966 | * | 3/1990 | |
| WO | WO9827411 | | 6/1998 | ............. G01L/9/00 |

* cited by examiner

*Primary Examiner*—Shelia V. Clark
(74) *Attorney, Agent, or Firm*—Cooper & Dunham LLP; Donald S. Dowden

(57) ABSTRACT

A sensor is described for measuring the parameters of a fluid, in particular for detecting substances in a gas. It comprises a measuring section (4) on a semiconductor chip (1), which is protected by a housing (3). A partition wall (12) of the housing (3) divides the semiconductor chip (1) into two parts (1a, 1b). The first part (1a) is connected to the outside by means of openings in the housing and carries the measuring section. The second part (1b) is covered by a hardened sealing material (11). The sealing material (11) protects the semiconductor chip (1) from undesired environmental influences. The dividing wall (12) forms a capillary between the chip and the housing, the capillary action of which draws in the sealing material and the end of which stops the sealing material.

16 Claims, 2 Drawing Sheets

SENSOR ACCOMMODATED IN A HOUSING

CROSS REFERENCE TO RELATED APPLICATIONS

This application claims the priority of Swiss patent application 2191/99, filed Nov. 30, 1999, the disclosure of which is incorporated herein by reference in its entirety.

BACKGROUND

The invention relates to a sensor for measuring parameters of a fluid, in particular for detecting substances in a gas, and a method for producing such a sensor according to the preamble of the independent claims.

STATE OF THE ART

Typical examples for sensors of this type are humidity sensors and $CO_2$ sensors. The packaging of such sensors in fairly complicated because, on the one hand, the sensor needs to be in contact with the medium to be measured while, on the other hand, it should be protected from the environment as well as possible.

BRIEF SUMMARY OF THE INVENTION

It is an object of the present invention to provide a sensor and a method, respectively, of the type mentioned initially, which alleviates this problem at least partially.

This object is achieved by the independent claims.

Hence, the housing of the sensor according to the invention is equipped with a barrier section, which extends towards the semiconductor chip and separates the same into two parts. The first part, where the actual measuring section of the semiconductor is located, is connected through at least one opening in the housing to the outside. In this part, which is in contact with the medium to be measured, the measurement can be carried out. The second part is covered at least partially, preferably completely, by a hardened sealing material, which protects the semiconductor chip in this part from environmental influences. The barrier section forms a barrier for the sealing material between the two parts. During production, the still liquid sealing material can be brought into the second part of the housing, wherein the barrier section prevents the material from entering the first part.

Preferably, the barrier section is a dividing wall, which can be straight, bent or angled.

Preferably, the barrier section approaches the semiconductor chip up to a thin gap, wherein the gap is filled with sealing material for providing a good sealing action. The width of the gap is preferably chosen such that the still liquid material is drawn in by capillary action during production.

The semiconductor chip is preferably arranged on a substrate, which is also, at least partially, in contact with the sealing material. In this manner the substrate can be connected to the housing. The sealing material can also be used for protecting the electrical connections or bond wires, respectively, between the semiconductor chip and the substrate and/or an integrated circuit on the substrate.

The housing can have various shapes. Preferably, it consists of conducting plastics or of plastics coated, by a conducting material for protecting the semiconductor chip from electric noise.

In the region of the second part the housing should have an opening for filling in the sealing material.

BRIEF DESCRIPTION OF THE DRAWINGS

Further embodiments, advantages and applications of the invention are given in the dependent claims as well as the now following description referring to the figures. These show:

DESCRIPTION OF THE INVENTION

Figure 1:
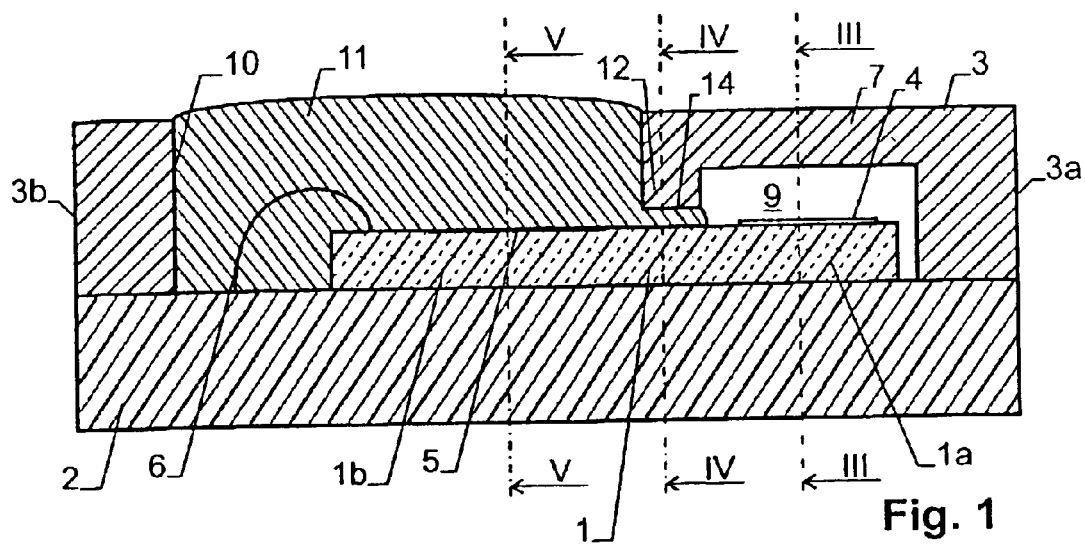
FIG. 1 a longitudinal section through an embodiment of a sensor according to the invention, FIG. 2 a top view of the sensor of FIG. 1, FIG. 3 a section along line III—III of FIG. 1, FIG. 4 a section along line IV—IV of FIG. 1, FIG. 5 a section along line V—V of FIG. 1, and FIG. 6 a partially cut view of several sensors prior to being sawed up.

In FIGS. 1 through 5 a preferred embodiment of a humidity sensor is shown. It comprises a semiconductor chip 1 lying on a substrate 2. A plastic housing 3 is arranged on substrate 2. For protecting semiconductor chip 1 from electric noise, the plastics can be weakly conducting or it can be coated with a conducting material.

A measuring section 4 is located on the semiconductor chip, e.g. consisting of a polymer layer or another humidity sensitive layer 1) between two electrodes, the electrical properties of which change depending on the humidity of the environment, or 2) on oscillating beam structures, the Eigenfrequency of which changes depending on the properties of the environment. Furthermore, an integrated circuit 5 is arranged on semiconductor chip 1, where a pre-processing or a complete processing of the measuring results takes place.

Semiconductor chip 1 is connected to substrate 2 by means of bond wires 6. The substrate is a printed circuit board. It carries, where applicable, devices for further processing the signals from semiconductor chip 1. Furthermore, it comprises conduits which lead to (now shown) contact pads at its bottom side.

Figure 2:
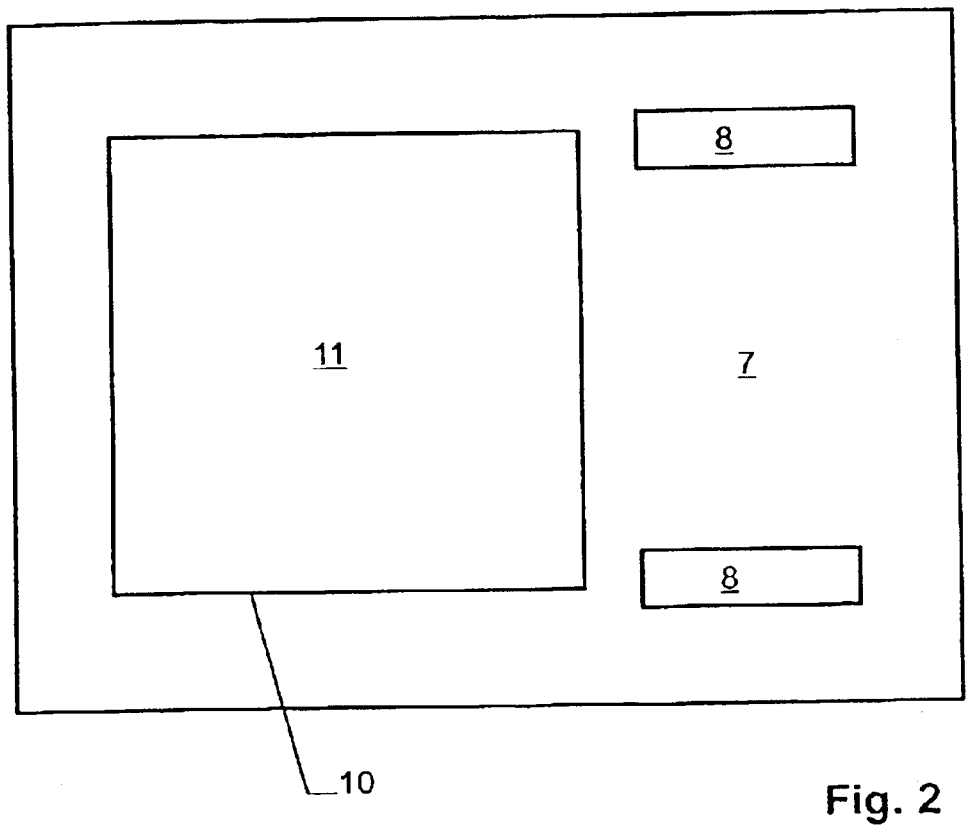
Figure 3:
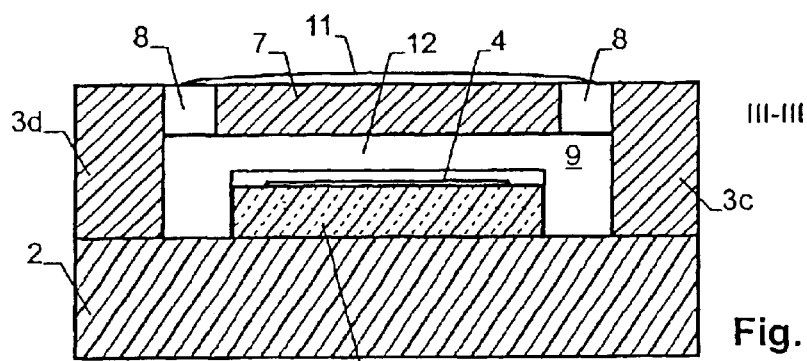
Figure 4:
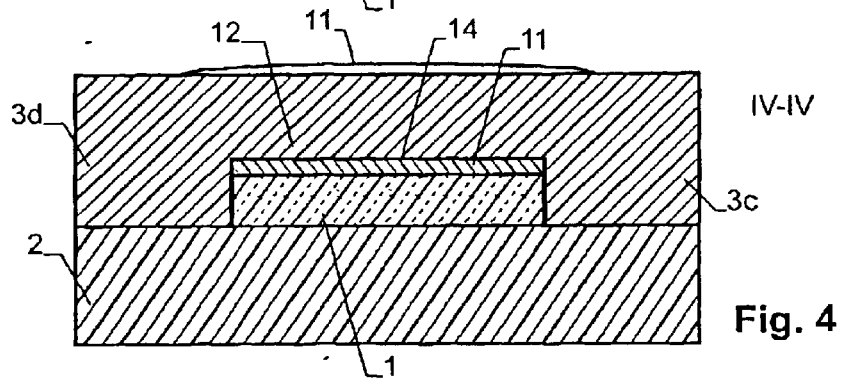
Figure 5:
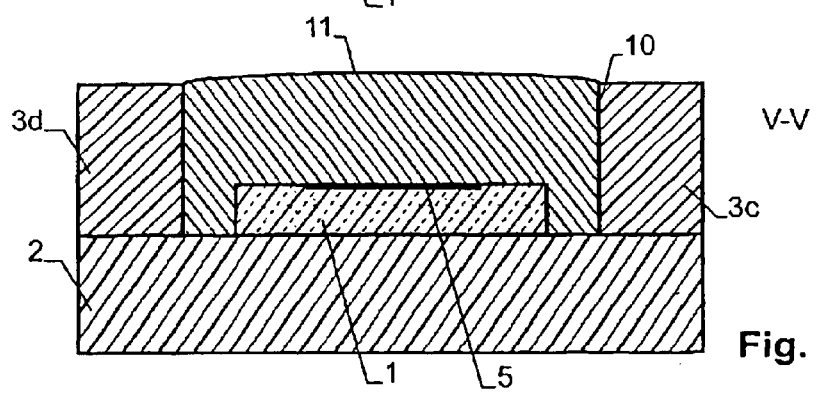

Substrate 2 and housing 3 have, as it is in particular shown in FIG. 2, a congruent, rectangular contour. Housing 3 comprises for side walls 3a, 3b, 3c, 3d, which rest on substrate 2 and extend around the outer edges of semiconductor chip 1. The right part of housing 3 in FIG. 1 is provided with a top wall 7 having two slit openings 8. The slit openings 8 connect a cavity 9 for receiving measuring section 4 under top wall 7 with the environment.

The left part of housing 3 in FIG. 1 comprises a large opening 10 for filling in a hardening sealing material 11, which covers or encloses part of semiconductor chip 1 and the bond wires 6 and protects the same. The sealing material further contacts housing 3 and substrate 2 and forms an adhesive connection between these two parts.

The left and the right part of the housing are divided by a partitioning wall 12, which is connected to top wall 7 and is somewhat set back when compared to the lateral walls 3c, 3d such that there is sufficient room for semiconductor chip 1 between partitioning wall 12 and the substrate. Partitioning wall 12 extends from above against semiconductor chip 1 and separates the same into a first (right) and a second (left) part 1a and 1b. In left part 1a there is measuring section 4, in right part 1b there is integrated circuit 5 and the contact pads for the bond wires 6. First part 1a borders cavity 9, second part 1b is covered by sealing material 11.

A thin gap extends between partitioning wall 12 and semiconductor chip 1. It is dimensioned such that it exerts a strong capillary force on the sealing material, which is still liquid during production, such that the same flows into gap 14. Gap 14 is, however, so thin that the strong change of the capillary force at the end of the barrier section prevents sealing material 11 from entering cavity 9.

Partitioning wall 12 therefore forms a barrier section of the housing, which keeps the sealing material away from the first section of the semiconductor.

Figure 6:
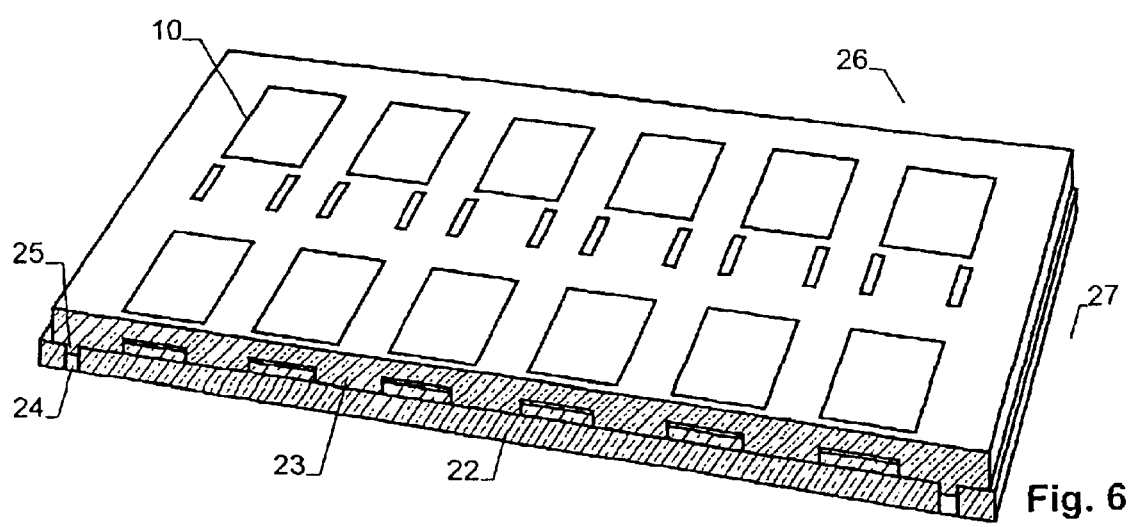

During production, as shown in FIG. 6, several sensors are produced at the same time. For this purpose, a substrate matrix 22 of several interconnected substrates 2 is used, onto which the semiconductor chips 1 and, where applicable, further devices are mounted at the predefined positions.

Then, a housing matrix 23 is set onto substrate matrix 22. Housing matrix 23 is e.g. an integral, injection cast part, where several housings 2 are pre-formed. Lateral guidance openings 24 and guidance pins 25 serve as positioning means for exactly positioning housing matrix 23 on substrate matrix 22.

Now, sealing material 11 is filled into the openings 10. During this, it is not necessary to observe the exact positioning of sealing material 11 because housing matrix 23, and in particular the partitioning walls 12, guide sealing material 11 to the appropriate places. In particular the variations of surface tension caused by the housing prevent an undesired covering of the sensor structure.

After hardening the sealing material, the sensors are ready. Before they are separated from each other, the whole sensor matrix shown in FIG. 6 is calibrated by being brought into a reference environment with now air humidity. Hence, a plurality of sensors can be calibrated in a single step.

Finally, the arrangement is sawed up such that the individual sensors are formed. Two of the corresponding saw lines 26, 27 are indicated in FIG. 6.

As mentioned initially, the present invention is not only suited for humidity sensors, but also for other types of sensors for measuring parameters of gases or liquids, such as $CO_2$ sensors.

While in the present application preferred embodiments of the invention are described, it is to be pointed out clearly that the invention is not limited to these and can also be carried out in different manner within the scope of the following claims.

What is claimed is:

1. A sensor for detecting substances in a gas, comprising a substrate,
   a semiconductor chip arranged on said substrate,
   a housing for protecting the semiconductor chip, said housing comprising a top wall, side walls extending transversely to the top wall and a barrier section extending as a partition wall between opposite side walls, wherein the barrier section extends towards the semiconductor chip and divides the semiconductor chip into at least a first and a second part, wherein the first part is connected with the outside through at least one opening in the housing,
   a measuring section arranged on the first part of the semiconductor chip and connected with an outside through said at least one opening,
   bond wires connecting said semiconductor chip to said substrate, and
   a hardened sealing material covering the second part at least partially, wherein said barrier section forms a barrier for the sealing material.

2. The sensor of claim 1 wherein the barrier section approaches the semiconductor chip up to a gap and wherein the gap is filled by the sealing material.

3. The sensor of claim 1 wherein the sealing material covers at least a part of the substrate.

4. The sensor of claim 3 wherein the sealing material connects the substrate to the housing.

5. The sensor of claim 3 wherein the sealing material covers bond wires between semiconductor chip and the substrate.

6. The sensor of claim 1 wherein the side walls are resting on a margin section of the substrate and at least a part of the barrier section is set back compared to the side walls for providing space for the semiconductor chip.

7. The sensor of claim 1 wherein the housing is a single part.

8. The sensor of claim 1 wherein the housing is of plastics and is coated by a conductive layer.

9. The sensor of claim 1 wherein the housing comprises a filling opening for the sealing material.

10. The sensor of claim 1 wherein the housing extends around outer edges of the semiconductor chip.

11. A method for producing a sensor wherein the sensor comprises a semiconductor chip having a measuring section and being protected by a housing, said method comprising the steps of
    arranging the semiconductor chip on a substrate and connecting the semiconductor chip with bond wires to the substrate,
    placing a housing over the semiconductor chip, wherein said housing comprises a top wall, side walls extending transversely to the top wall and a barrier section formed by a partitioning wall between opposite side walls, wherein the barrier section extends towards the semiconductor chip and divides the semiconductor chip into a first and a second part, wherein the first part is connected through an opening in the housing to an outside and carries the measuring section,
    covering the second part at least partially by a hardening sealing material while using said barrier section for preventing the sealing material from flowing into the first part.

12. The method of claim 11 wherein the hardening sealing material is brought into a gap between the barrier section and the semiconductor chip by means of capillary forces.

13. The method of claim 11 wherein several semiconductor chips are arranged on a substrate matrix and that a housing matrix of several, interconnected housings is brought onto the semiconductor chips, wherein in the area of each sensor sealing material is introduced, and wherein the substrate matrix is cut up together with the housing matrix for forming the individual sensors.

14. The method of claim 13 characterized in that the sensors are brought into a reference environment and calibrated before being cut up.

15. The sensor of claim 1 wherein an integrated circuit is arranged on the semiconductor chip.

16. The sensor of claim 1 wherein the housing is of conducting plastics.

* * * * *